(12) United States Patent
Zhao et al.

(10) Patent No.: US 11,399,933 B2
(45) Date of Patent: Aug. 2, 2022

(54) CARDIAC VALVE PROSTHESIS AND STENT THEREOF

(71) Applicant: SHANGHAI MICROPORT CARDIOFLOW MEDTECH CO., LTD., Shanghai (CN)

(72) Inventors: Chunxia Zhao, Shanghai (CN); Ming Yang, Shanghai (CN); Guoming Chen, Shanghai (CN); Yu Li, Shanghai (CN)

(73) Assignee: SHANGHAI MICROPORT CARDIOFLOW MEDTECH CO., LTD., Shanghai (CN)

( * ) Notice: Subject to any disclaimer, the term of this patent is extended or adjusted under 35 U.S.C. 154(b) by 34 days.

(21) Appl. No.: 16/958,518

(22) PCT Filed: Nov. 23, 2018

(86) PCT No.: PCT/CN2018/117163
§ 371 (c)(1),
(2) Date: Jun. 26, 2020

(87) PCT Pub. No.: WO2019/128583
PCT Pub. Date: Jul. 4, 2019

(65) Prior Publication Data
US 2021/0052379 A1    Feb. 25, 2021

(30) Foreign Application Priority Data
Dec. 28, 2017    (CN) .......................... 201711467178.7

(51) Int. Cl.
A61F 2/24    (2006.01)

(52) U.S. Cl.
CPC .......... *A61F 2/2418* (2013.01); *A61F 2/2409* (2013.01); *A61F 2/2427* (2013.01);
(Continued)

(58) Field of Classification Search
CPC .................................................... A61F 2/2418
See application file for complete search history.

(56) References Cited

U.S. PATENT DOCUMENTS

| 5,080,668 A | 1/1992 | Bolz et al. |
| 2011/0208297 A1 | 8/2011 | Tuval et al. |

(Continued)

FOREIGN PATENT DOCUMENTS

| CN | 102438546 A | 5/2012 |
| CN | 104000672 A | 8/2014 |

(Continued)

*Primary Examiner* — Suba Ganesan
(74) *Attorney, Agent, or Firm* — Muncy, Geissler, Olds & Lowe, P.C.

(57) ABSTRACT

The present application relates to a cardiac valve prosthesis and a stent thereof. The stent comprises an inflow channel, an outflow channel, and a transitional area between the inflow channel and the outflow channel along an axial direction; the outflow channel comprises a cyclic structure and at least two convex structures extending along the axial direction; the at least two convex structures are respectively connected to the end of the cyclic structure distant from the transitional area; a restricted vacant area is formed between adjacent convex structures. The cardiac valve prosthesis and the stent thereof are not only suitable for multiple types of valve replacement, risks of injuries and operation costs are reduced for patients, and the influence of the stent to cardiac functions is minimized.

12 Claims, 8 Drawing Sheets

(52) U.S. Cl.
   CPC ........... *A61F 2220/0016* (2013.01); *A61F 2220/0075* (2013.01)

(56) References Cited

U.S. PATENT DOCUMENTS

| | | |
|---|---|---|
| 2012/0101571 A1 | 4/2012 | Thambar et al. |
| 2013/0073035 A1* | 3/2013 | Tuval ............... A61F 2/2418 623/2.11 |
| 2016/0113764 A1 | 4/2016 | Sheahan et al. |
| 2017/0042673 A1* | 2/2017 | Vietmeier ........... A61F 2/2418 |
| 2017/0100236 A1* | 4/2017 | Robertson .......... A61F 2/2418 |
| 2018/0125651 A1* | 5/2018 | Nasr ................ A61F 2/2412 |

FOREIGN PATENT DOCUMENTS

| | | |
|---|---|---|
| CN | 107088112 A | 8/2017 |
| WO | WO-2015126712 A1 | 8/2015 |
| WO | WO-2015/128747 A2 | 9/2015 |

\* cited by examiner

CARDIAC VALVE PROSTHESIS AND STENT THEREOF

TECHNICAL FIELD

The present application relates to the field of medical instruments and, in particular, to a heart valve prosthesis and a stent thereof.

BACKGROUND

The heart has four chambers: the left atrium and ventricle on the left side of the heart; and the right atrium and ventricle on the right side of the heart. In addition, the ventricular inflow tract is formed between the atria and the corresponding ventricle, the left ventricular outflow tract is formed between the left ventricle and aorta and the right ventricular outflow tract is formed between the right ventricle and pulmonary artery. In order to ensure the normal flow of blood in those chambers, there are also "one-way valves" in the ventricular inflow and outflow tracts. Defects in these valves can induce hemodynamic changes and functional abnormalities of heart that are called valvular heart diseases.

With the development of social economy and the aging of population, the incidence of valvular heart diseases has increased significantly. Studies have shown that this figure has reached up to 13.3% among the aged people of 75 years or older. Surgical treatment remains the first choice for patients with severe valvular diseases. However, for those with advanced ages, complications in multiple organs, a history of thoracotomy or poor heart functions, the surgical approach is associated with high risk and high mortality or even precludes some patients. Transcatheter valve replacement/repair offers advantages such as no need for thoracotomy, minor trauma and rapid recovery.

The native heart valves' structure varies with their location. For this reason, valve prostheses used in interventional transcatheter valve replacement/repair procedures have to address various anatomies and pathological needs.

The valves in the left and right ventricle inflow tracts are mitral and tricuspid, respectively, and are each an assembly including the annulus, leaflets, chordae tendineae, papillary muscles (and also including the ventricular wall in some literatures). The chordae tendineae lies between the leaflets and ventricular wall to serve as a support portion connecting the mitral (or tricuspid) leaflets and the myocardium. The anterior mitral annulus is an extension of the non-coronary and left annuli of the aortic valve. During replacement with a prosthetic valve, an inappropriate stent design tends to lead to obstructions of the left ventricular outflow tract.

The valves in left and right ventricular outflow tracts are the aortic and pulmonary valves, respectively, which differ from those in the ventricular inflow tracts in only consisting of the leaflets and annulus. The native structures surrounding the aortic valve in the left ventricular outflow tract is complicated, and there are openings of the left and right coronary arteries on the outflow tract side of the leaflets. Therefore, an inappropriate stent design is likely to lead to fatal complications such as obstructions of the coronary artery openings.

Among the above-described heart valves, the aortic and mitral valves are more prone to abnormalities. Since the two valves have different surrounding cardiac structures, interventional replacement of them takes different sets of factors into consideration and generally uses distinct artificial valves. For a patient who needs to replace both valves, separate delivery systems and typically separate implantation procedures are therefore required, leading to a long treatment cycle, a high patient cost, an increased intraoperative risk and a high risk of vascular damage due to the multiple establishments of implantation channels.

SUMMARY

Technical Problem

On this basis, there is a need to provide a heart valve prosthesis and a stent thereof aiming at the problem that the current commercially available interventional valve prostheses are not adaptable to various valves and require separate delivery systems and separate implantation procedures.

Solution to the Problem

Technical Solution

A stent for a heart valve prosthesis, the stent having a contracted configuration and an expanded configuration, where the stent comprises, along an axis direction of the stent, an inflow tract, an outflow tract and an intermediate section between the inflow and outflow tracts. The outflow tract comprises an annular structure and at least two protrusions each formed by extending along the axis direction of the stent. The at least two protrusions are each connected to one end of the annular structure away from the intermediate section. Vacant areas are defined between adjacent protrusions.

The above stent includes, along its axis, the inflow tract, the outflow tract and the intermediate section between the inflow and outflow tracts, the outflow tract including the annular structure and at least two protrusions formed by extending along the axis direction of the stent. Each protrusion is connected to one end of the annular structure away from the intermediate section and a vacant area is defined between adjacent protrusions. The protrusions not only contribute to providing a space for suturing leaflets in a valve assembly onto the stent, but the vacant area defined by the protrusions is able to minimize the adverse impact on the heart's functions. Moreover, the vacant areas are absent of stent mesh cells and a skirt, which allows reducing overall filling dimension of the outflow tract after the heart valve prosthesis is loaded in a delivery system. Hence, this decreases the required size of the delivery system, thereby enabling the stent suitable for use in the replacements of multiple types of valves such as the aortic and mitral valves, while not requiring multiple delivery systems or multiple implantation procedures.

In one embodiment, three protrusions are provided and the three protrusions are distributed uniformly around a circumference of the annular structure.

In one embodiment, the outflow tract further comprises suture rods connected to one end of a corresponding protrusion away from the intermediate section.

In one embodiment, each of the at least two protrusions has a triangular structure comprising one or more structural cells, which are arranged into one or more rows.

In one embodiment, each of the at least two protrusions is rod-shaped.

In one embodiment, the intermediate section has an inwardly concave profile when the stent is in the expanded configuration.

In one embodiment, each of the at least two protrusions has a stiffness gradually descending along a direction from the intermediate section to the outflow tract.

In one embodiment, the stent further comprises barbs circumferentially distributed on the intermediate section and/or the outflow tract, the barbs extending outwardly from the intermediate section or the outflow tract.

In one embodiment, the outflow tract has an axial height of 5-30 mm.

In one embodiment, in the expanded configuration, the intermediate section has a minimum diameter not greater than a minimum diameter of the inflow tract and a maximum diameter not greater than a maximum diameter of the outflow tract.

In one embodiment, the stent further comprises lugs arranged on one end of the inflow tract away from the intermediate section and/or one end of the outflow tract away from the intermediate section.

A heart valve prosthesis comprises a valve assembly and the stent as defined above, in which the valve assembly is attached to the stent.

Beneficial Effect of the Application

Beneficial Effect

The above heart valve prosthesis is adaptable to multiple valves and the corresponding interventional valve replacement.

EMBODIMENTS

Embodiments

As mentioned in the Background, present application provides a heart valve prosthesis and a stent thereof aiming at the problem that the current commercially available interventional valve prostheses are not adaptable to various valves and thus require separate delivery systems and separate implantation procedures.

After further researches, in one embodiment, there is provided a stent for a heart valve prosthesis. The stent is configured to support an artificial heart valve. The stent comprises, along an axis direction of the stent, an inflow tract, an outflow tract and an intermediate section between the inflow and outflow tracts. The stent has a contracted configuration and an expanded configuration. The outflow tract includes an annular structure and at least two protrusions formed by extending along the axis direction of the stent. The at least two protrusions are each connected to one end of the annular structure away from the intermediate section and define vacant areas between adjacent protrusions.

Further, On the basis of the above stent, there is also provided a heart valve prosthesis for replacing a native heart valve.

Specific embodiments of present application will be described in detail below in conjunction with the accompany drawings to make the above objects, features and advantages of the present application more apparent and readily understood.

Figure 1:
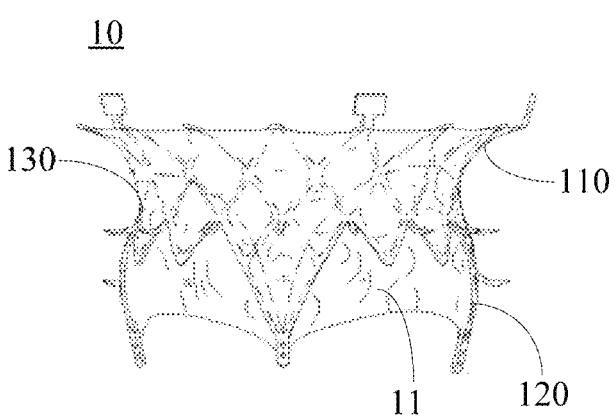
FIG. 1 is a structural schematic diagram of a stent of a first embodiment that has been used in a heart valve prosthesis.
Figure 2:
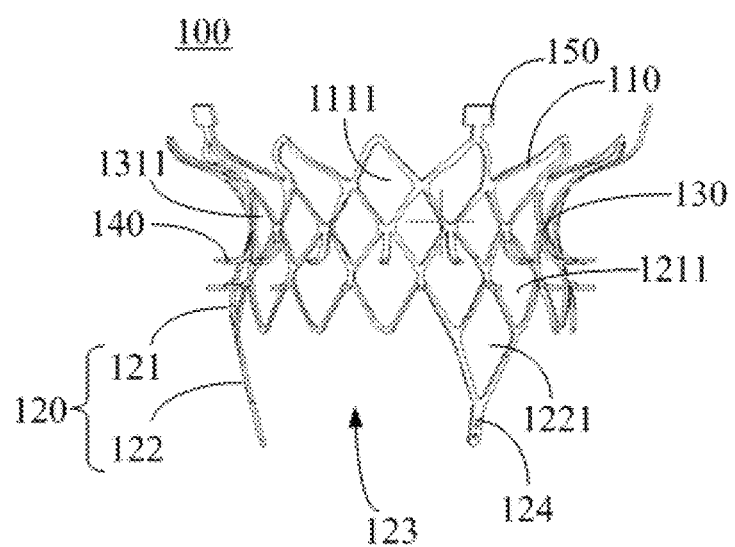
FIG. 2 is a structural schematic diagram of the stent of FIG. 1.

As shown in FIG. 1 and FIG. 2, a stent 100 for a heart valve prosthesis 10 according to embodiment 1 includes, along an axis thereof, an inflow tract 110, an outflow tract 120 and an intermediate section 130. The stent 100 has a contracted configuration for delivery and an expanded configuration for deployment. The stent 100 is configured to support an artificial heart valve (that is, a valve assembly 11), and constitutes said heart valve prosthesis 10 together with the valve assembly 11. The intermediate section 130 is disposed between the inflow tract 110 and the outflow tract 120. Depending on the flow direction of blood, the outflow tract 120 is disposed downstream of the inflow tract 110.

In one embodiment, the stent 100 may be a self-expandable stent including a plurality of structural cells, which are interconnected to form a mesh. The stent 100 is fabricated from a biocompatible material such as a titanium alloy or a nickel-titanium alloy. It is noted that the structural cells refer to mesh cells made of a biocompatible material such as a titanium alloy or a nickel-titanium alloy and in the shape of diamonds, pentagons, triangles, teardrops or the like. The structural cells include first structural cells configured to form the outflow tract 120, second structural cells configured to form the inflow tract 110 and third structural cells configured to form the intermediate section 130. In other embodiments, the stent 100 may be a balloon-expandable stent including a plurality of structural cells in a mesh form.

As shown in FIG. 2, the outflow tract 120 has a mesh structure consisting of one or more rows of first structural cells. The plurality of first structural cells interconnect along a circumference of the stent 100 to form a row, and multiple rows of first structural cells interconnect along an axis direction of the stent 100. The first structural cells may be in the shape of diamonds, pentagons, triangles, teardrops or other closed loops. In this embodiment, the first structural cells may be diamonds. It should be noted that the number of mesh loops may depend on an actually needed axial height of the outflow tract 120.

When the stent 100 is released, the outflow tract 120 is located on a hemodynamic outflow side of the native valve. In one embodiment, the outflow tract 120 in the stent 100 may have an axial height of 5-30 mm.

Referring again to FIG. 2, the outflow tract 120 may be a spherical structure. That is, the outflow tract 120 extends from its end connected to the intermediate section 130 away from the intermediate section 130 by a certain radius, i.e., radially outward from a center axis of the stent 100.

It should be noted that, in other embodiments, the outflow tract 120 may be in the shape of a truncated cone. That is, the end of the outflow tract 120 proximal to the intermediate section 130 has a diameter greater than the end of the outflow tract 120 distal from the intermediate section 130. That is, the diameter of the outflow tract 120 decreases gradually in a direction extending axially away from the intermediate section 130.

The outflow tract 120 includes the annular structure 121 and protrusions 122 formed by extending along the axial direction. The number of the protrusions may be two or more. Each of the protrusions 122 is connected to the end of the annular structure 121 away from the intermediate section 130, and the vacant areas 123 are defined between adjacent protrusions 122. These vacant areas 123 can minimize any adverse influence on the heart's functions. Moreover, the vacant areas are absent of stent mesh cells (structural cells) and a skirt, which allows to reduce overall filling dimension of the outflow tract after the heart valve prosthesis 10 is loaded into a delivery system, thus reducing a required footprint of the delivery system and making the stent suitable for use in the replacements of multiple types of valves, such as the aortic and mitral valves. In addition, the protrusions 122 contribute to providing a space for suturing leaflets in the valve assembly onto the stent 100, so that the sutured leaflets are not affected by the surrounding tissue.

One end of the annular structure 121 in the outflow tract 120 is connected to the end of the intermediate section 130 away from the inflow tract 110, while the other end of the annular structure 121 is connected to a protrusion 122. As noted above, the outflow tract 120 may be implemented as a mesh structure composed of one or more rows of first structural cells. As shown in FIG. 2, the first structural cell includes a first sub-structural cell 1211 and a second sub-structural cell 1221. In this case, the annular structure 121 is constructed by the one or more rows of first sub-structural cells 1211 that are sequentially connected along the circumferential direction. The annular structure 121 provides sufficient support for the outflow tract of the stent 100 and sufficient counter-traction for the leaflets. In one embodiment, the outflow tract 120 has a maximum diameter of 21-56 mm.

In one embodiment, the number of the protrusions 122 is three, and the three protrusions 122 are uniformly distributed along the circumferential direction of the annular structure 121. That is, the three protrusions 122 are uniformly distributed with a circumferential angle of 120°. Since the coronary sinus ostium in the aortic valve has a distribution of about 120° and the anterior mitral annulus accounts for one third of the annulus perimeter, by providing three protrusions 122, the stent 100 can be used for both aortic and mitral valves. In this way, for patients in need of replacing both valves, only one suitable delivery system is required to achieve replacements of two valves through a same implantation channel, and there is no need to implant different valve prostheses in two separate implantation procedures, which allow to save treatment time and costs and reduce risk of vascular damages incurred by the multiple establishments of implantation channels. It should be noted that, since the tricuspid valve is anatomically similar to the mitral valve, the stent can also be used for tricuspid valve replacement. In one embodiment, as shown in FIG. 2, the outflow tract 120 may also include suture rods 124, the suture rod connected to one end of a respective protrusion 122 away from the intermediate section 130 and configured to attach the leaflets. It should be noted that holes may be formed in the suture rod 124, through which the leaflets in the valve assembly can be sutured onto the stent 100. Alternatively, the leaflets may be attached to the suture rods 124 using an adhesive. The present application is not limited to any particular method for attaching the leaflets to the suture rods 124.

Figure 11:
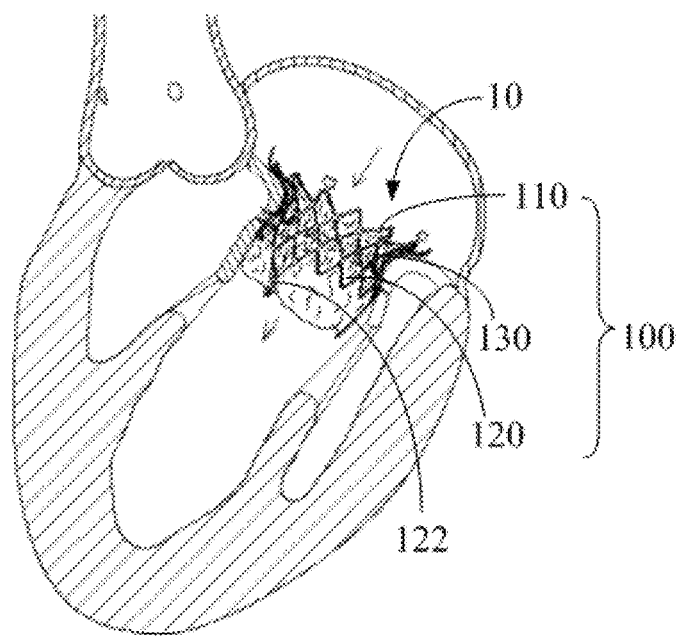
FIG. 11 is a structural schematic diagram of an embodiment of a heart valve prosthesis during a diastolic phase of the heart, when replacing the native mitral valve.
Figure 12:
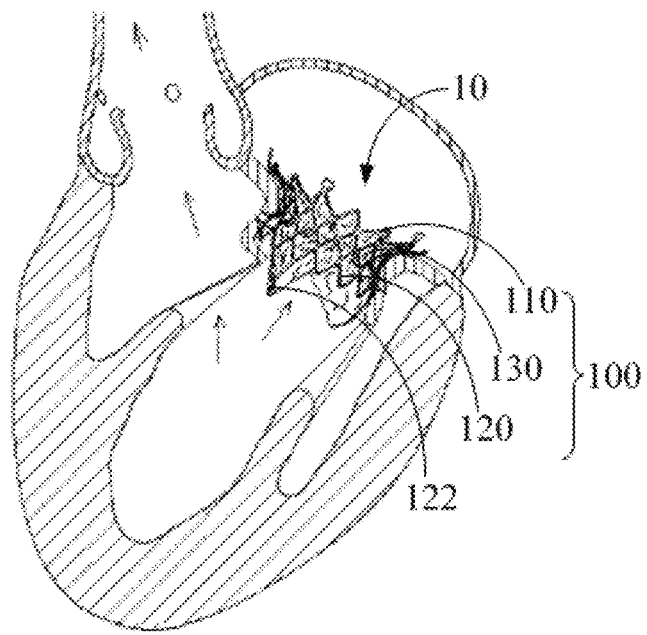
FIG. 12 is a structural schematic diagram of the heart valve prosthesis of FIG. 11 during a systolic phase of the heart, when replacing the native mitral valve.

In one embodiment, in the direction from the intermediate section 130 to the outflow tract 120, each protrusion 122 has a stiffness gradually descending in order to accommodate varying traction forces at different locations of the stent applied by the leaflets in the heart valve prosthesis 10, thus helping in extending the stent's serve life. As shown in FIG. 11, the end of a leaflet of the heart valve prosthesis attached to both the intermediate section 130 and outflow tract 120 is the attachment end and the other end of the leaflet of the heart valve prosthesis not connected to the stent is the free end. The inventors have found from researches that, during opening of the leaflets in the heart valve prosthesis 10 under the action of blood flow, the aligned leaflets will be increasingly separated apart from one another radially while gradually moving axially away from the intermediate section 130 in the blood flow direction, until the aligned leaflets are fully opened, where the free end of each leaflet is farthest away from the stent's center axis. On the other hand, as shown in FIG. 12, the leaflets of the heart valve prosthesis 10 are subjected to a pressure towards the inflow tract 110 of the stent due to the back-pressure of blood, which causes the leaflets of the heart valve prosthesis 10 to move radially towards the center axis of the stent and move axially towards inflow tract 110 of the stent. When leaflets of the heart valve prosthesis 10 are fully closed, free ends of multiple adjacent leaflets closely fit each other while axial displacements of their free ends towards the inflow tract 110 of the stent are occurred.

As a bearing member of the leaflets of the heart valve prosthesis 10 during the movements, the stent 100 reciprocates circumferentially and axially with the opening and closing of the leaflets of the heart valve prosthesis 10. That is to say, the closing of the leaflets of the heart valve prosthesis 10 causes protrusions 122 of the stent 100 to deform radially towards the center axis of the stent and to deform axially towards the intermediate section 130 of the stent 100, in order to resist the pressure of blood. On the other hand, while the leaflets are open, protrusions 122 of the stent 100 gradually recover their normal shapes due to the shape memory nature of the stent 100. Due to the inherent design characteristics of the leaflets of the heart valve prosthesis 10, from the free end to the attachment end, the area of each leaflet of the heart valve prosthesis 10 subjected to the back-pressure of blood in the axial direction gradually decreases, and hence the back-pressure of blood applied to each leaflet gradually decreases due to the constant blood pressure. As a result, the tractions of the leaflets applied to respective locations of the stent 100 substantially present a trend of axially ascending gradually from the intermediate section 130 to the outflow tract 120, and thus the protrusion 122, along the said direction, should have a stiffness decreasing gradually and a flexibility ascending gradually. In this way, when the leaflets are closed, the stiffer portions of the stent 100 serve as portions of the stent 100 providing higher deformation resistances, while the less stiff portions of the stent 100 serve as portions of the stent 100 having large deformations with the deformation of the leaflets. Thus, the protrusions 122 of the stent 100 have a reduced risk of fracture and an extended fatigue lifetime.

In the case that the outflow tract 120 is implemented as a spherical structure, the annular structure 121 is provided at a proximal end of the spherical structure, while the suture rods 124 are provided at a distal end of the spherical structure. It should be noted that the proximal and distal ends are mentioned here with respect to the direction of blood flow, which flows from the proximal end towards the distal end.

Referring again to FIG. 2, in one embodiment, the protrusion 122 is formed by one or more rows of the second sub-structural cells 1221. The large vacant areas 123 absent of any aforementioned structural cell is defined between protrusions 122. In this embodiment, one protrusion 122 is a triangular structure extending away from the intermediate section 130 and composed of one second sub-structural cell 1221. It should be noted that the second sub-structural cells 1221 may assume either the same shape as or a different shape from the first sub-structural cells 1211.

In one embodiment, any of the protrusions 122 may be a part of a sphere, a cone or a cylinder, and may be a planar triangle or any other shape, as long as it extends from the annular structure 121 along the direction away from the intermediate section 130. Further, all of the protrusions 122 may be of the same shape and size. It should be noted that each of the protrusions 122 may be of a different shape and size. It is also possible that some of them are of the same shape and size but some of them have different shapes and sizes from the others.

Referring again to FIG. 1 and FIG. 2, in one embodiment, the inflow tract 110 includes mesh structures composed of one or more rows of second structural cells 1111. The inflow tract 110 is fabricated from a shape memory and biocompatible tube by cutting, for example, the cold laser cutting. It should be noted that the intermediate section 130 and outflow tract 120 can be fabricated by a same cutting method. In addition, the inflow tract 110, outflow tract 120 and intermediate section 130 may be integrally formed. It should be noted that the second structural cells 1111 of the inflow tract 110 may be mesh cells that can form closed shapes, such as diamonds, pentagons, triangles, teardrops or the like, or may be rods. In addition, the inflow tract 110 may be formed by weaving with filaments. In one embodiment, the weaving filaments may be woven into a sinusoidal or zigzag pattern.

Figure 3:
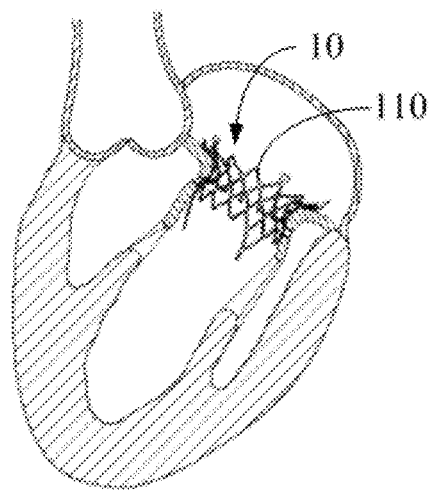
FIG. 3 is a structural schematic diagram of the stent of FIG. 1 used to replace a native mitral value.
Figure 4:
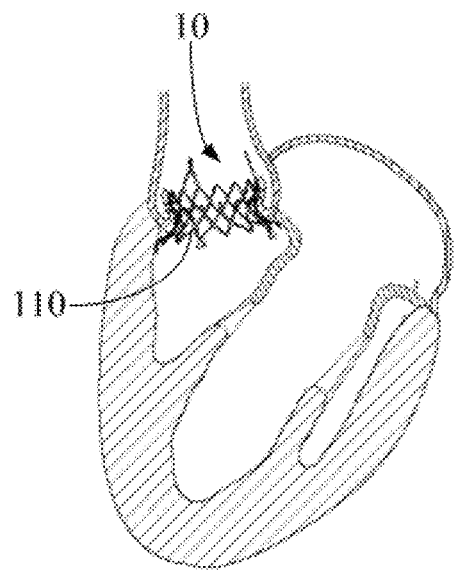
FIG. 4 is a structural schematic diagram of the stent of FIG. 1 used to replace a native aortic value.

When the stent 100 is used for the aortic and mitral valves and after release of the stent 100, the inflow tract 110 is located at a hemodynamic inflow side of the native valve and fits tissues around the annulus of the native valve. Specifically, as shown in FIG. 3, when the heart valve prosthesis 10 using the stent 100 is used to replace the native mitral valve, the inflow tract 110 covers the left atrioventricular ostium. When the heart valve prosthesis 10 using the stent 100 is used to replace the native aortic valve, the inflow tract 110 covers the base of the aortic sinus, as shown in FIG. 4.

In one embodiment, the shaped of the radial cross-section of the inflow tract 110 may be annulus, D-shaped or flower-shaped or other irregular shape. In order to ensure the inflow of blood, from the end of the inflow tract 110 connected to the intermediate section 130, the inflow tract 110 extends axially away from the intermediate section 130. In other words, the attachment end of the inflow tract 110 to the intermediate section 130 extends outward away from the intermediate section 130 along the axial direction. In another embodiment, from the end of the inflow tract 110 connected to the intermediate section 130, the inflow tract 110 both axially and radially extends away from the intermediate section 130. In still other embodiments, from the end of the inflow tract 110 connected to the intermediate section 130, the inflow tract 110 only radially extends away from the intermediate section 130.

Further, in order to prevent dislodgement of the heart valve prosthesis of the stent 100, the inflow tract 110 has a minimum diameter greater than the native valve annulus. In one embodiment, the minimum diameter of the inflow tract 110 ranges from 25 mm to 65 mm.

As shown in FIG. 1, the inflow tract 110 may extend from the connection connected to the intermediate section 130 by an axial height H of 0-20 mm away from the intermediate section 130. Here, when the height H is equal to 0 mm, the inflow tract 110 of the stent 100 only radially extends away from its connection connected to the intermediate section. That is, all structural cells in the inflow tract 110 lie in the same plane.

Figure 5:
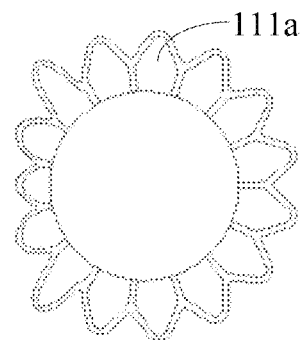
FIG. 5 is a structural schematic diagram of an embodiment of an inflow tract of FIG. 1.
Figure 6:
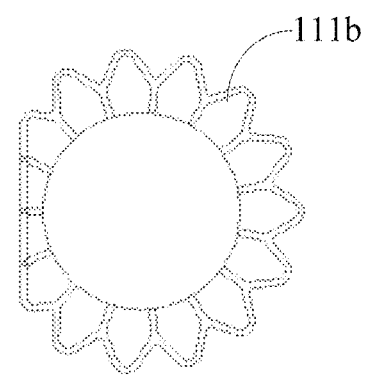
FIG. 6 is a structural schematic diagram of another embodiment of the inflow tract of FIG. 1.

In one embodiment where the inflow tract 110 has a D-shaped radial cross-section, the inflow tract 110 includes a plurality of first constituent cells 111a, the plurality of first constituent cells 111a having different mesh sizes, so that formed inflow tract 110 has a varying diameter along varying directions of its radial cross-section, as shown in FIG. 5. In other embodiments, as shown in FIG. 6, the inflow tract 110 includes a plurality of equally-sized second constituent cells 111b, the plurality of second constituent cells 111b having a same mesh size. In this case, some second constituent cells 111b have their axial length longer than the remaining second constituent cells 111b, so that formed inflow tract 110 has a varying diameter along varying directions of its radial cross-section. It should be noted that the first and second constituent cells 111a, 111b are different implementations of the structural cells that constitute the inflow tract 110.

Specifically, when the heart valve prosthesis 10 incorporating the stent 100 is used to replace the native aortic valve, the flat portion of the D-shaped inflow tract can be brought into close contact with the left coronary sinus of the native aortic valve, greatly reducing the risk of left bundle branch block around the left coronary sinus caused by the stent 100. Likewise, when the heart valve prosthesis 10 incorporating the stent 100 is used to replace the native mitral valve, the flat portion of the D-shaped inflow tract can be brought into close contact with the native aortic valve, thus avoiding the heart valve prosthesis 10 from impairing the functions of the native aortic valve and reducing the risk of obstruction of the left ventricular outflow tract.

In case of the inflow tract 110 having a radial cross-section that is annular, as shown in FIG. 2, the inflow tract 110 includes a plurality of equally-sized second structural cells 1111 having the same axial height H, so that the inflow tract 110 has a constant radial diameter. That is, the inflow tract 110 is a cylindrical structure. In this case, the cross-sectionally annular inflow tract 110 extends radially away from the intermediate section 130 and axially away from the outflow tract 120. In this way, the inflow tract 110 is prevented from damaging the heart tissue due to an excessive radial dimension.

Specifically, when the heart valve prosthesis 10 is used to replace the native aortic valve, the inflow tract 110 covers the base of the aortic sinus while extending towards the left ventricle. When the heart valve prosthesis 10 is used to replace the native mitral valve, the inflow tract 110 covers the atrioventricular orifice while extending towards the left atrium.

In an alternative embodiment, the inflow tract 110 may be a spherical structure. That is to say, as the height of the inflow tract 110 axially extending away from the transition area 130 increases, the diameter of the radial cross-section of the inflow tract 110 gradually increases and then gradually decreases. It should be noted that the inflow tract 110 may also be in the shape of a truncated cone with a gradually increasing diameter as the inflow tract 110 axially extends away from its connection connected to the intermediate section 130.

In this embodiment, the stent 100 has a contracted configuration for delivery and an expanded configuration for deployment. In the expanded configuration, the intermediate section 130 has an inwardly concave profile fitting with the native annulus. This can help in positioning of the stent 100 and providing the stent 100 with an anchoring force. Accordingly, in one embodiment, the intermediate section 130 has a minimum diameter not greater than the minimum diameter of the inflow tract 110 and a maximum diameter not greater than the maximum diameter of the outflow tract 120, so that the stent 100 is inwardly concave at the intermediate section 130 on the whole. After release of the stent 100, the intermediate section 130 fits the native annulus to provide stent 100 with radial support. The inwardly concave structure not only helps in positioning of the heart valve prosthesis 10 but also decreases axial movement or displacement of the stent 100 to a certain extent.

Referring to FIG. 2, the intermediate section 130 has a mesh structure including one or more rows of third structural cells 1311. In one embodiment, the third structural cells 1311 in the intermediate section 130 may be in the shape of diamonds. It should be noted that the application is not limited to any particular shape of the third structural cells 1311 in the intermediate section 130, and the structural cells may also have a triangular or any other suitable shape. In one embodiment, the intermediate section 130 may have an axial height of 3-15 mm.

In one embodiment, the intermediate section 130 may be stiffer than both the inflow tract 110 and the outflow tract 120 in order to further provide radial support to the stent 100. It should be noted that the stiffness of material of the intermediate section 130 is higher than that of material of both the inflow tract 110 and outflow tract 120 to offer the intermediate section 130 a greater stiffness, or the more compact structure of the intermediate section 130 offers itself a greater stiffness.

The intermediate section 130 fits the native annulus after release of the stent 100. Therefore, the minimum diameter of the intermediate section 130 is greater than the diameter of the native annulus. In one embodiment, the minimum diameter of the intermediate section 130 ranges from 20 mm to 58 mm.

It should be noted that the first structural cells, second structural cells 1111 and third structural cells 131 may be either of the same shape or of different shapes, which can be determined depending on the actual needs.

For patients with valve stenosis, the stent 100 of the heart valve prosthesis 10 could be anchored with the aid of the radial support provided by the inwardly concave structure formed at the intermediate section 130. For regurgitation patients, the heart valve prosthesis 10 is design to unilateral passive open in the blood flow direction and unilateral passive close against the blood flow direction. In this design, blood constantly pushes against the leaflets in the heart valve prosthesis 10 during closing of the leaflets, thus avoiding axial displacement of the heart valve prosthesis 10 over time due to insufficient anchoring force.

Accordingly, in one embodiment, as shown in FIGS. 1 and 2, the stent 100 may further include barbs 140 projecting outwardly from the intermediate section 130 or from the outflow tract 120. That is to say, barbs 140 extend radially along the direction away from the stent 100. The barbs 140 may be distributed circumferentially across both the intermediate section 130 and the outflow tract 120. In this case, barbs 140 can be arranged into one or more rows. It should be noted that, in case of the barbs 140 distributed on the outflow tract 120, they can be distributed on the annular structure 121 of the outflow tract 120, which can further provide the annular structure 121 with an anchoring force. In other embodiments, the barbs 140 may be circumferentially distributed only on the intermediate section 130. Alternatively, the barbs 140 may be circumferentially distributed only on the outflow tract 120.

The barbs 140 outwardly projecting from the stent 100 so as to pierce the native valve's leaflets and annulus, providing an anchoring force to the heart valve prosthesis 10. In this way, the barbs 140 and inwardly concave profile together provide the anchoring force to the stent 100 to avoid movement or displacement of the stent 100. Further, due to the anchoring force provided by the barbs 140, anchoring support required by the stent 100 at the native annulus can be reduced, thus avoiding rupture of the native annulus.

Figure 7:
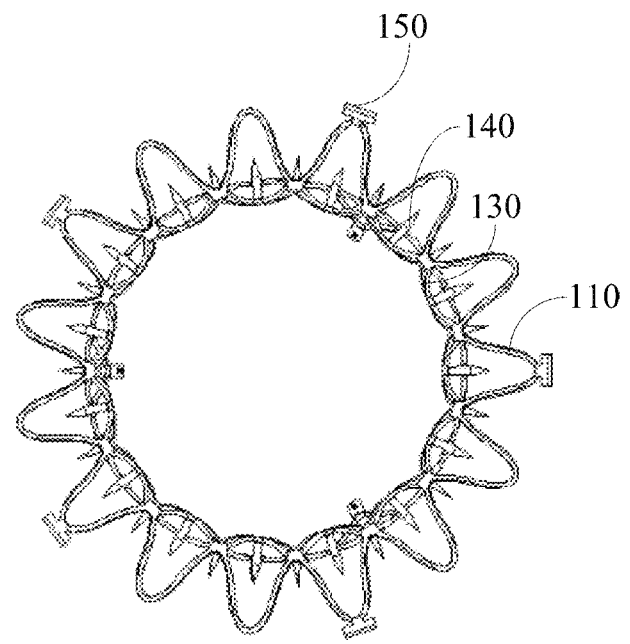
FIG. 7 is a top view of the stent of FIG. 1.

Specifically, as shown in FIG. 7, each barb 140 may have a proximal end connected to a node of the mesh structure of the intermediate section 130 or outflow tract 120 and a distal end having a triangular, a tapered shape or other shape that can facilitate to pierce tissues.

In one embodiment, each barb 140 extends both radially and axially with respect to the intermediate section 130 or outflow tract 120. That is, each barb 140 extends away from the intermediate section 130 or outflow tract 120 at an angle with respect to the intermediate section 130 or outflow tract 120. In one embodiment, each barb 140 forms an angle of 20-160° with a normal of an outer surface of the intermediate section 130 or outflow tract 120 at a node of the stent. Here, the "stent node" refers to a junction of the barb 140 with the outer surface of the intermediate section 130 or outflow tract 120. Alternatively, the barb 140 may extend radially away from the node.

Further, in one embodiment, the barbs 140 may extend away from the intermediate section 130 or outflow tract 120 along the radial direction of the intermediate section 130 or outflow tract 120 and extend axially towards the inflow tract 110. Specifically, with the barbs 140 distributed on the intermediate section 130 as an example, the barbs 140 each form an angle with the outer surface of the intermediate section 130 and have an end portion pointing toward the inflow tract 110. Likewise, the barbs 140 may be distributed on the outflow tract 120 in the same manner.

It should be noted that each barb 140 may consist of two portions connected to each other. One of two portions may extend in a manner in consistent with radial extension of the intermediate section 130 and have a square or trapezoid cross-sectional shape, while the other portion may have a curved cross-sectional shape. In one embodiment, the center of the curved cross-section is located at the side where the inflow tract 110 is situated.

Alternatively, the barb 240 having a configuration of two portions may have a configuration of a combination of an arc portion and a straight portion. In this case, the arcuate portion is connected to the intermediate section 130 or outflow tract 120 at one end and to the straight portion at the other end, and the straight portion is tangential to the arcuate portion.

As shown in FIG. 2, in one embodiment, the cross section of the barb structure 140 in the radial direction may also be a curved surface that extending from the junction of the barb 140 with the intermediate section 130 or outflow tract 120. It should be noted that each barb 140 may having a configuration of a combination of multiple curved segments.

In one embodiment, the barb 140 extends a radial length of 0.5-6 millimeters (mm) away from the intermediate section 130 or outflow tract 120. That is, when the barb 140 is arranged on the intermediate section 130, there may be a perpendicular distance of 0.5-6 mm from the end of the barb 140 away from the intermediate section 130 to the end of the barb 140 connected to the intermediate section 130. Similarly, when the barb 140 is arranged on the outflow tract 120, there may also be a perpendicular distance of 0.5-6 mm from the end of the barb 140 away from the outflow tract 120 to the end of the barb 140 connected to the outflow tract 120.

In one embodiment, the barbs 140 and the outflow tract 120 are integrally formed. Alternatively, the barbs 140 and the intermediate section 130 may be integrally formed. Alternatively, the barbs 140, intermediate section 130 and outflow tract 120 may be integrally formed. It should be noted that such integral formation can be achieved by a cutting technique. In other embodiments, the barbs 140 may be fixedly coupled to the outflow tract 120, for example, by welding, riveting, or the like. Likewise, the barbs 140 may be alternatively fixed to the intermediate section 130 by welding or riveting or otherwise.

In one embodiment, the stent 100 further includes lugs 150 for fitting the heart valve prosthesis 10 with a delivery system for delivering the heart valve prosthesis 10. The lugs 150 are attached to the delivery system to ensure a constant relative position between the heart valve prosthesis 10 and the delivery system in the courses of the heart valve prosthesis 10 being loaded within the delivery system, released from the delivery system and delivered by the delivery system within the body. Depending on the implantation method of the heart valve prosthesis 10 and the function of the delivery system, the lugs 150 may be arranged at the end of the inflow tract 110 away from the intermediate section 130, or arranged at the end of the outflow tract 120 away from the intermediate section 130. Still, the lugs 150 may also be arranged at the end of the inflow tract 110 away from the intermediate section 130, and the end of the outflow tract 120 away from the intermediate section 130. The number and locations of the lugs 150 may be determined depending on the actual needs.

The lugs 150 are the final portions of the heart valve prosthesis 10 detached from the delivery system. Specifically, in the case that the lugs 150 are arranged at the end of the inflow tract 110 away from the intermediate section 130, the outflow tract 120 will be released first during the release. In the case that the lugs 150 are arranged on the end of the outflow tract 120 away from the intermediate section 130, the inflow tract 110 will be released first during the release. In the case that the lugs 150 are arranged at both the end of the inflow tract 110 away from the intermediate section 130 and the end of the outflow tract 120 away from the intermediate section 130, the release process is a two-way release process which can be performed by release the lugs 150 on either end first or release the lugs 150 on both ends at the same time finally.

Figure 8:
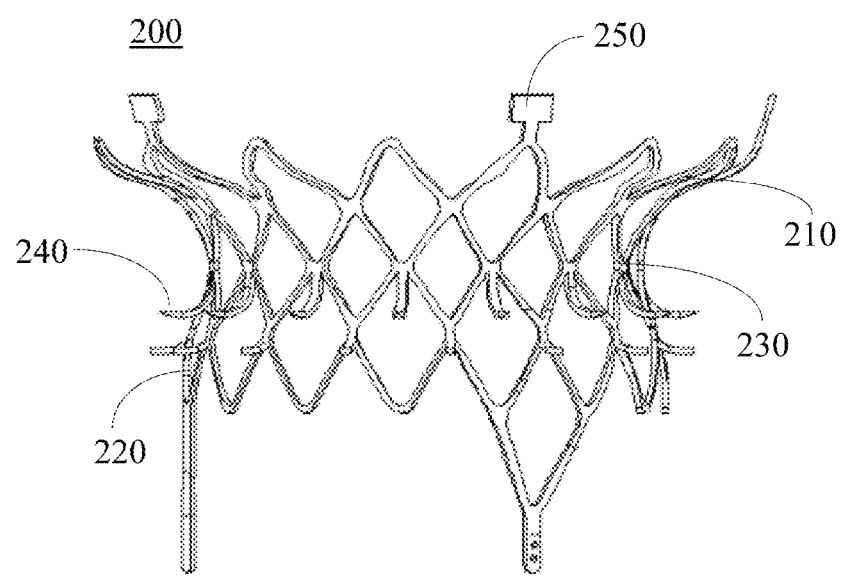
FIG. 8 is a structural schematic diagram of a stent according to a second embodiment.

As shown in FIG. 8, a stent 200 according to a second embodiment includes an inflow tract 210, an outflow tract 220, an intermediate section 230, barbs 240 and lugs 250. The structures of these components in the stent 200, as well as the connections therebetween and the like, are the same as those in the first embodiment and will not be again described here. The stent 200 differs from the stent 100 according to the first embodiment in that the outflow tract 220 is cylindrical. That is, the outflow tract 220 extends axially from its end connected to the intermediate section 230 away from the intermediate section 230 with a constant diameter.

Figure 9:
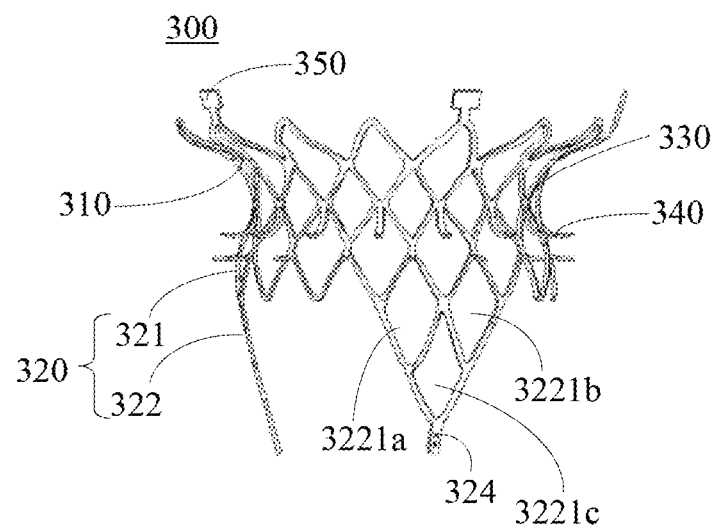
FIG. 9 is a structural schematic diagram of a stent according to a third embodiment.

As shown in FIG. 9, a stent 300 according to a third embodiment includes an inflow tract 310, an outflow tract 320, an intermediate section 330, barbs 340 and lugs 350. The structures of these components in the stent 300, as well as the connections therebetween and the like, are the same as those in the first embodiment and will not be again described here. The stent 300 differs from the stent 100 according to the first embodiment in that each protrusion 322 has a triangular structure extending away from the intermediate section 330. The triangular structure includes a plurality of second sub-structural cells, each implemented as a mesh cell. The plurality of second sub-structural cells are arranged into multiple rows. In this embodiment, three second sub-structural structural cells are provided and arranged into two rows. Referring again to FIG. 9, the three second sub-structural cells are a first cell 3221a, a second cell 3221b and a third cell 3221c. The first and second cells 3221a, 3221b are connected to each other and are each connected at one end to the annular structure 321. One end of the third cell 3221c is connected to the ends of the first and second cells 3221a, 3221b away from the annular structure 321. The other end of the third cell 3221c away from the annular structure 321 is connected to a suture post 324. It should be noted that the multiple cells may be arranged in to a single row. In other embodiments, the multiple cells may be arranged into three or more rows. In addition, the number of the second sub-structural cells may be two, four or more, which is not limited here.

Figure 10:
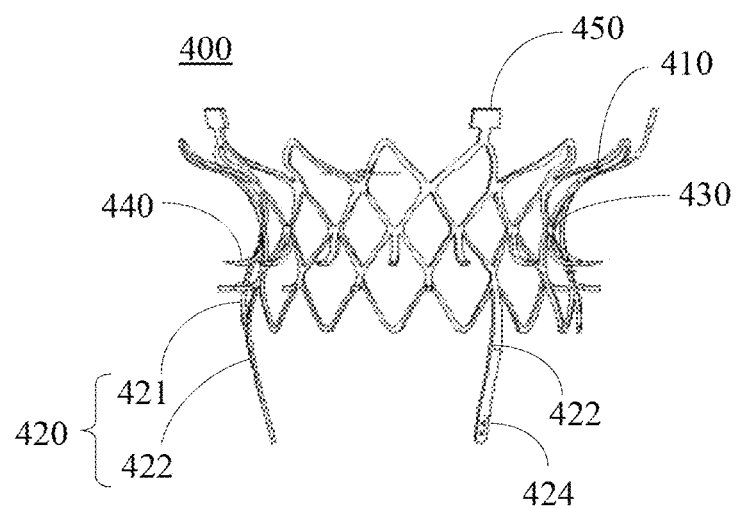
FIG. 10 is a structural schematic diagram of a stent according to a forth embodiment.

As shown in FIG. 10, a stent 400 according to a fourth embodiment includes an inflow tract 410, an outflow tract 420, an intermediate section 430, barbs 440 and lugs 450. The structures of these components in the stent 400, as well as the connections therebetween and the like, are the same as those in the first embodiment and will not be again described here. The stent 400 differs from the stent 100 according to the first embodiment in that each protrusion 422 is rod-shaped structure. One end of the protrusion 422 is connected to the end of the annular structure 421 away from the intermediate section 430, and the other end of the protrusion 422 away from the annular structure 421 is connected to a suture post 424. It should be noted that each protrusion 422 may also include a plurality of second sub-structural cells, each implemented as rod-shaped structure and connected sequentially.

As shown in FIG. 1, the heart valve prosthesis 10 according to an embodiment includes a valve assembly 11 and the stent according to any of the above embodiments, the valve assembly 11 attached to the inside of the stent. Specifically, the valve assembly 11 may include leaflets and a skirt. The leaflets are attached to both the intermediate section and the outflow tract, with the skirt being attached to the inflow tract, intermediate section and the outflow tract, in order to ensure the single blood flow channel and prevent perivalvular leakage.

Since the outflow tract includes protrusions and vacant areas and has leaflets sutured at its inner side, the radial diameter of the stent decreases and the axial height of the stent increases after the heart valve prosthesis 10 is loaded into the delivery system. Moreover, since the vacant areas are absent of mesh cells of the stent and a skirt, the space is saved and the diameter of outflow tract in the contracted configuration of the heart valve prosthesis 10 is reduced, thereby reducing the required diameter of the delivery system and risk of vascular damage during delivery.

Since the heart valve prosthesis 10 is suitable for use in the replacement of both the aortic and mitral valves, it is possible that such prosthesis may be used to replace the aortic or mitral valve separately, or two such prostheses may be used to successively replace valves in two locations through two times of successive loading of the two prostheses into a same delivery system and two times of successive delivering of the two prostheses in a single implantation channel, thus shortening the time and incisions required by channel establishment, lowering the risk of injury to the patient and bringing down the cost of surgery. It is also possible that two such prostheses may be used to successively replace valves in two locations through one time of delivering of the two prostheses using one delivery system. In this case, two heart valve prostheses 10 are loaded into the delivery system at the same time, and are replaced one by one. This can additionally shorten the surgical time and lower the risk of vascular damage during delivery.

Specifically, when the heart valve prosthesis 10 is used to replace a native mitral valve, the vacant areas correspond to the anterior leaflet side of the native mitral valve. As shown in FIG. 11, during a diastolic phase of the heart, the leaflets of the heart valve prosthesis 10 are opened naturally by the blood wash. During a systolic phase of the heart, blood flows from the ventricle to the aorta. At this time, the aortic valve is opened and the heart valve prosthesis 10 that replaces the native mitral is closed, as shown in FIG. 12. The path of blood flowing out of the left ventricle is called the left ventricular outflow tract, and the anterior leaflet side of the native value faces this left ventricular outflow tract. When the stent in the heart valve prosthesis 10 that replaces the native mitral valve has a low height at its subvalvular portion facing the left ventricular outflow tract, it can prevent the left ventricular outflow tract from being blocked to cause malfunction of the heart. There are vacant areas defined in the outflow tract of the stent in the heart valve prosthesis 10, so that when the vacant areas face the anterior leaflet side of the native valve, the height of the subvalvular portion of the stent facing the left ventricular outflow tract is low. This allows preventing obstruction of the left ventricular outflow tract due to an excessive subvalvular length of the stent on the premise of an ensured normal operation of the heart valve prosthesis 10. It should be noted that the arrows in FIG. 11 and FIG. 12 indicate the direction of blood flow.

Figure 13:
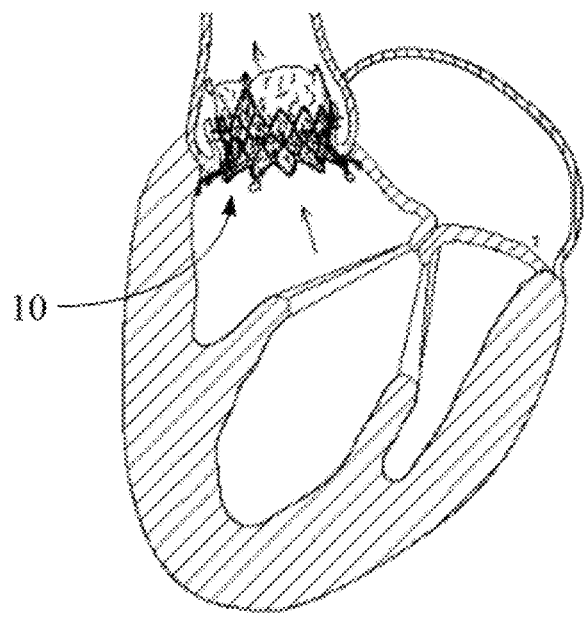
FIG. 13 is a structural schematic diagram of the heart valve prosthesis of FIG. 11 during a systolic phase of the heart, when replacing the native aortic valve.
Figure 14:
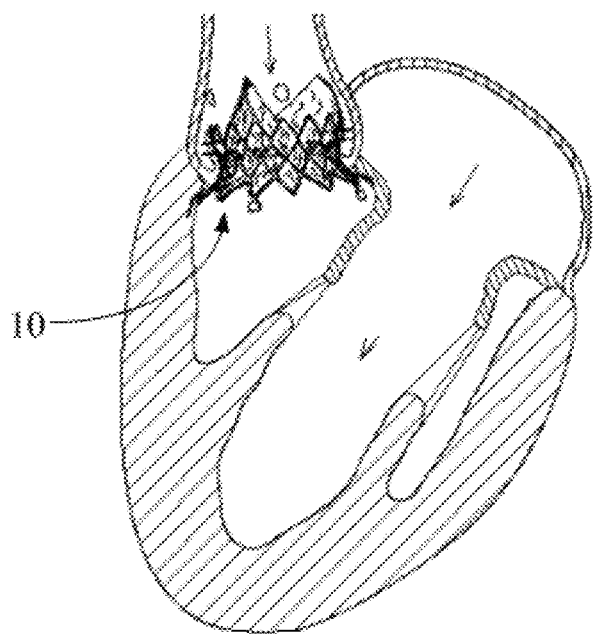
FIG. 14 is a structural schematic diagram of the heart valve prosthesis of FIG. 11 during a diastolic phase of the heart, when replacing the native aortic valve.

When the heart valve prosthesis 10 is used to replace the native aortic valve, the vacant areas correspond to the coronary sinus ostia. During the heart beating, the left coronary ostium is located in the left aortic sinus and the right coronary ostium is located in the right aortic sinus, an angle of about 120° formed between the left and right coronary ostia. Since the stent of the heart valve prosthesis 10 is uniformly and circumferentially distributed with an angle of 120°, the stent of the heart valve prosthesis 10 will not block the coronary ostia at all. As shown in FIG. 13, when the heart contracts, the leaflets of the heart valve prosthesis 10 will be opened naturally by the blood wash, and the blood flows from the left atrium into the ascending aorta. During a diastolic phase of the heart, since the blood pressure in the aorta will be higher than that in the ventricle, the leaflets close under the blood pressure while blood enters into the coronary artery via the coronary ostia, as shown in FIG. 14. It should be noted that the arrows in FIG. 13 and FIG. 14 indicate the direction of blood flow.

The above-described stent includes, along its axis direction, the inflow tract, the outflow tract and the intermediate section between the inflow and outflow tracts and has the contracted configuration for delivery and the expanded configuration for deployment. In the expanded configuration of the stent, the intermediate section has an inwardly concave profile that fits the anatomy of the native valve annulus, thereby helping in positioning of the stent and providing the stent with an anchoring force. The outflow tract includes an annular structure and at least two protrusions formed by the axial extension, the at least two protrusions each connected to the end of the annular structure away from the intermediate section and defines vacant areas between adjacent protrusions. These protrusions not only provide a space for suturing the leaflets in the valve assembly onto the stent, but also the defined vacant areas minimize the adverse impact on the heart's functions. Meanwhile, since the vacant areas are absent of mesh cells of stent and a skirt, which allows reducing overall filling dimension of the outflow tract after the heart valve prosthesis is loaded in a delivery system. Hence, this decreases the required size of the delivery system, thereby enabling the stent suitable for use in the replacements of multiple types of valves such as the aortic and mitral valves.

The features of the above-described embodiments may be combined arbitrarily. While not all possible combinations of these features are described for the sake of brevity, they are all considered within the scope of this specification as long as there is no contradiction therein.

The foregoing embodiments represent merely a few embodiments of the present application, and have been described above specifically and in detail. However, they are not intended to be understood as limiting the scope of the application. It is noted that, many variations and modifications can be made by those of ordinary skill in the art without departing from the spirit of the present application, which all fall into the protection scope of the application as defined by the appended claims.

What is claimed is:

1. A stent for a heart valve prosthesis, the stent having a contracted configuration and an expanded configuration, wherein the stent comprises, along an axis direction of the stent, an inflow tract, an outflow tract and an intermediate section between the inflow tract and outflow tract, the outflow tract comprising an annular structure, a plurality of suture rods and at least two protrusions each formed by extending along the axis direction of the stent, the annular structure constructed by one or more rows of first structural elements that are sequentially connected along a circumferential direction of the stent, each protrusion connected to a corresponding suture rod at an end away from the intermediate section and connected to corresponding adjacent first structural elements at an end close to the intermediate section, wherein a vacant area is defined between adjacent protrusions and adjacent protrusions do not have a connection, wherein each protrusion has a stiffness gradually descending along a direction from the intermediate section to the outflow tract.

2. The stent of claim 1, wherein three protrusions are provided, the three protrusions distributed uniformly around a circumference of the annular structure.

3. The stent of claim 1, wherein each protrusion has a triangular structure comprising one or more rows of second structural cells, each protrusion extending from terminals of adjacent first structural elements in the row of first structural elements closest to the outflow tract.

4. The stent of claim 1, wherein each protrusion is rod-shaped and extends from a connection of adjacent first structural elements in the row of first structural elements closest to the outflow tract.

5. The stent of claim 1, wherein the intermediate section has an inwardly concave profile when the stent is in the expanded configuration.

6. The stent of claim 1, further comprising barbs circumferentially distributed on the intermediate section and/or the outflow tract, the barbs formed by extending outwardly from the intermediate section or the outflow tract.

7. The stent of claim 1, wherein the outflow tract has an axial height of 5-30 mm.

8. The stent of claim 1, wherein in the expanded configuration, the intermediate section has a minimum diameter not greater than a minimum diameter of the inflow tract and a maximum diameter not greater than a maximum diameter of the outflow tract.

9. The stent of claim 1, further comprising lugs arranged on one end of the inflow tract away from the intermediate section and/or one end of the outflow tract away from the intermediate section.

10. A heart valve prosthesis, comprising a valve assembly and a stent as defined in claim 1, the valve assembly attached to the stent.

11. The stent of claim 1, wherein the stent is suitable for replacements of both aortic and mitral valves.

12. The stent of claim 1, wherein the vacant area between adjacent protrusions has a circumferential width defined by a plurality of circumferentially arranged first structural elements.

\* \* \* \* \*